US006937900B1

(12) United States Patent
Pianca et al.

(10) Patent No.: US 6,937,900 B1
(45) Date of Patent: Aug. 30, 2005

(54) AC/DC MULTI-AXIS ACCELEROMETER FOR DETERMINING PATIENT ACTIVITY AND BODY POSITION

(75) Inventors: Anne M. Pianca, Valencia, CA (US); Gene A. Bornzin, Simi Valley, CA (US); Euljoon Park, Stevenson Ranch, CA (US); Alan B. Vogel, Saugus, CA (US); Joseph J. Florio, La Canada, CA (US); Lee Jay Mandell, West Hills, CA (US); Junyu Mai, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 448 days.

(21) Appl. No.: 10/205,188

(22) Filed: Jul. 24, 2002

Related U.S. Application Data

(63) Continuation of application No. 09/457,451, filed on Dec. 8, 1999, now Pat. No. 6,466,821.

(51) Int. Cl.$^7$ .............................................. A61N 1/372
(52) U.S. Cl. .......................................... 607/19; 607/18
(58) Field of Search ...................................... 607/17–19

(56) References Cited

U.S. PATENT DOCUMENTS

| 5,031,615 | A | | 7/1991 | Alt |
| 5,074,302 | A | | 12/1991 | Poore et al. |
| 5,330,510 | A | | 7/1994 | Legay et al. |
| 5,342,404 | A | | 8/1994 | Alt et al. |
| 5,354,317 | A | | 10/1994 | Alt |
| 5,476,483 | A | | 12/1995 | Bornzin et al. |
| 5,514,162 | A | | 5/1996 | Bornzin et al. |
| 5,593,431 | A | * | 1/1997 | Sheldon ........................ 607/19 |
| 5,725,562 | A | | 3/1998 | Sheldon |
| 5,833,713 | A | | 11/1998 | Moberg |
| 5,865,760 | A | | 2/1999 | Lidman et al. |
| 6,044,297 | A | * | 3/2000 | Sheldon et al. ................ 607/17 |
| 6,466,821 | B1 | * | 10/2002 | Pianca et al. .................. 607/18 |

* cited by examiner

*Primary Examiner*—George R. Evanisko

(57) ABSTRACT

An implantable cardiac stimulation device which determines stimulation based upon the patient's body position and activity level while eliminating special implantation or calibration procedures. To eliminate such special implantation and calibration procedures, the stimulation device correlates the patient's body position using a multi-axis DC accelerometer or other sensor during times of high activity and determines a patient's standing position value. During other times, the stimulation device compares the signals from the accelerometer to the standing position value to determine the patient's current body position. Based upon the current body position and the activity level, the stimulation device determines the necessary stimulation to deliver to the patient.

18 Claims, 10 Drawing Sheets

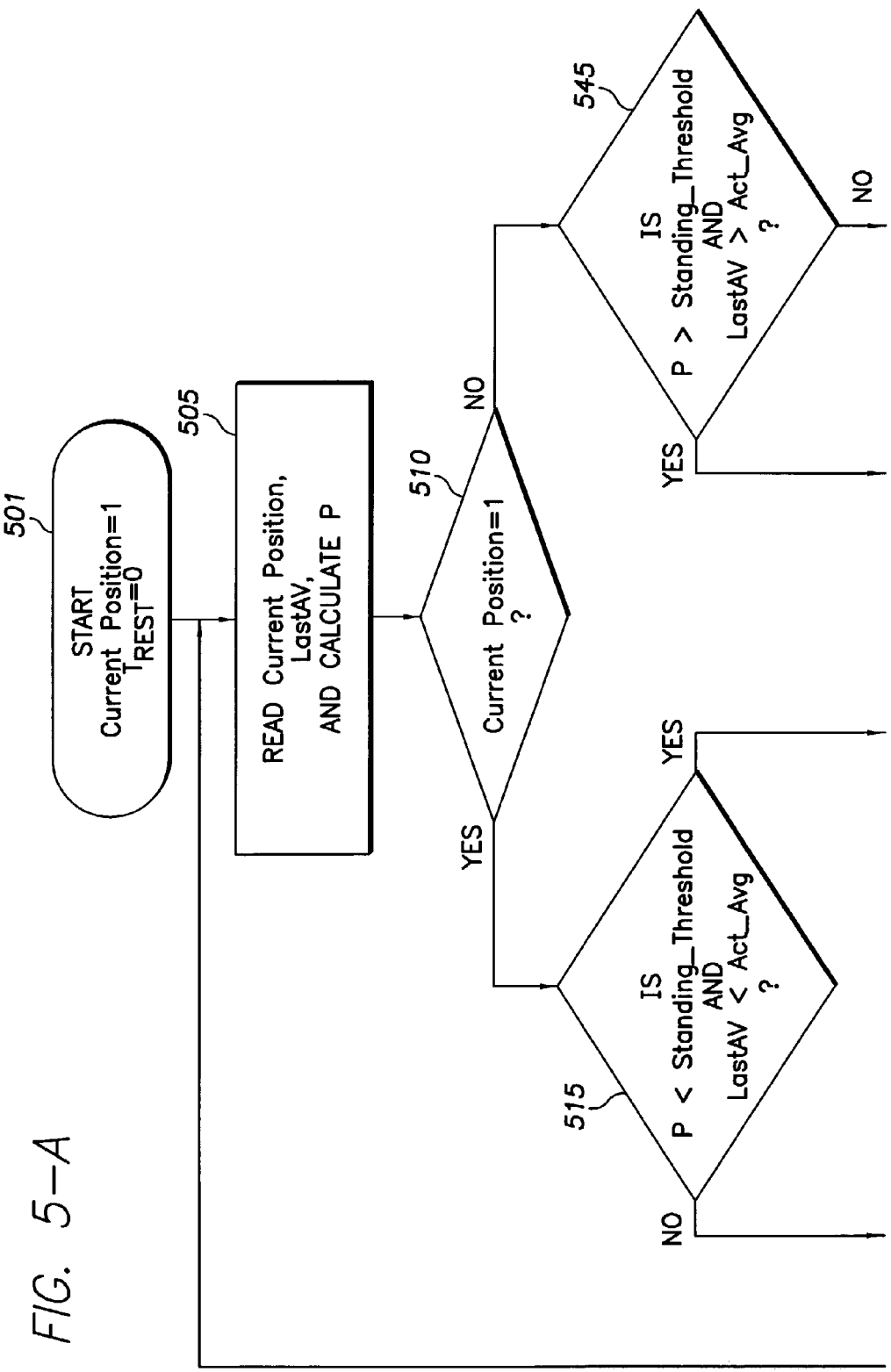
FIG. 5-A

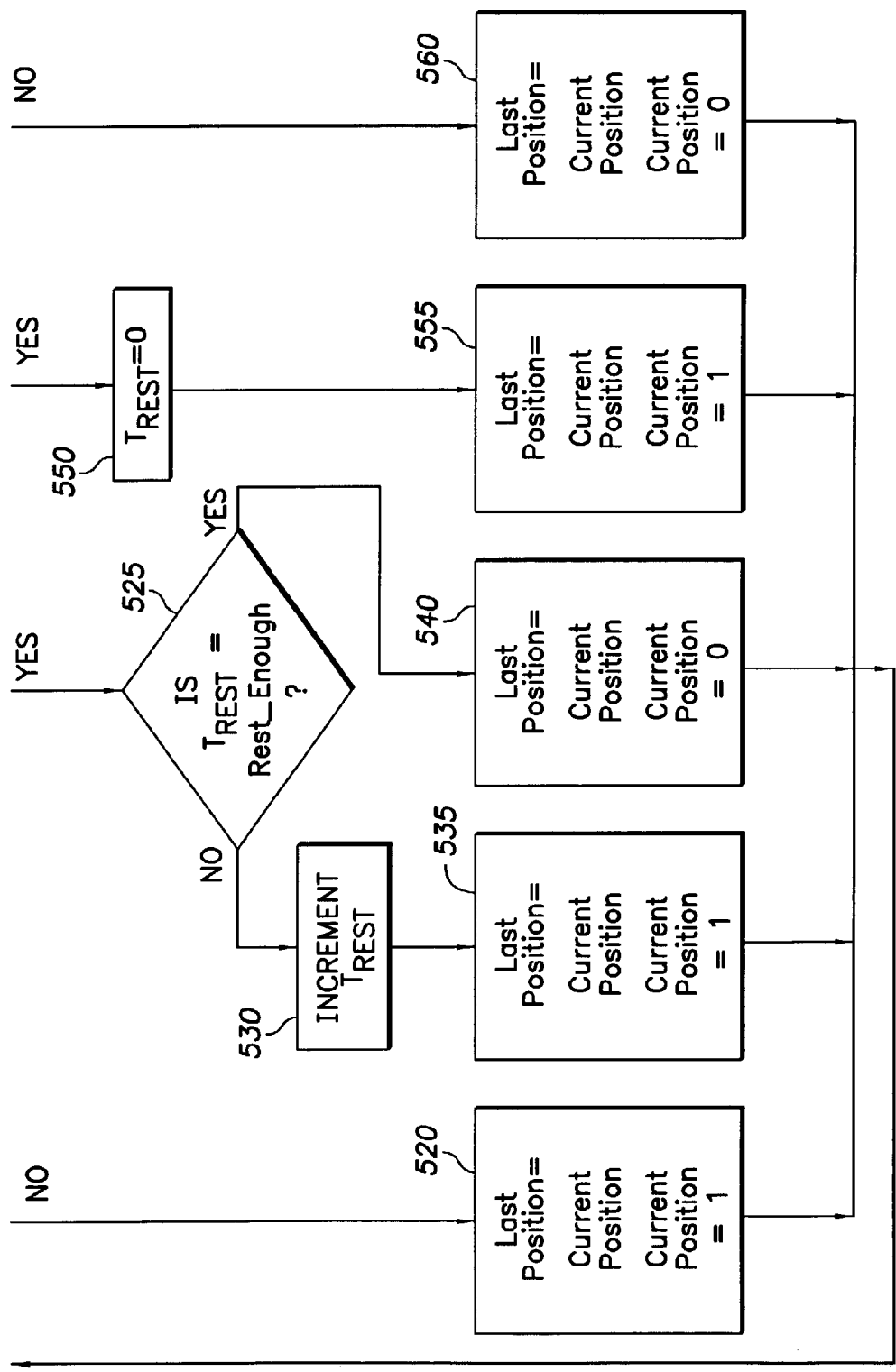
FIG. 5-B

AC/DC MULTI-AXIS ACCELEROMETER FOR DETERMINING PATIENT ACTIVITY AND BODY POSITION

CROSS-REFERENCE TO RELATED APPLICATIONS

This application is a continuation of U.S. patent application Ser. No. 09/457,451, filed Dec. 8, 1999, now U.S. Pat. No. 6,466,821.

FIELD OF INVENTION

This invention relates to cardiac stimulators which use indicators of patient activity and body position to determine the type and intensity of cardiac stimulation.

BACKGROUND OF THE INVENTION

The class of medical devices known as cardiac stimulation devices can deliver and/or receive electrical energy from the cardiac tissue in order to prevent or end life debilitating and life threatening cardiac arrhythmias. Pacing delivers relatively low electrical stimulation pulses to cardiac tissue to relieve symptoms associated with a slow heart rate, an inconsistent heart rate, an ineffective heart beat, etc. Defibrillation delivers higher electrical stimulation pulses to cardiac tissue to prevent or end potentially life threatening cardiac arrhythmias such as ventricular fibrillation, ventricular tachycardia, etc.

Early advances in pacing technology have led to a better quality of life and a longer life span. The development of demand pacing, in which the stimulator detects the patient's natural cardiac rhythm to prevent stimulation during times which the patient's heart naturally contracts, led to a more natural heart rate as well as a longer battery life.

Another major advance was rate responsive pacing in which the stimulator determines the stimulation rate based upon the patient's metabolic demand to mimic a more natural heart rate. The metabolic demand typically is indicated by the patient's activity level via a dedicated activity sensor, minute ventilation sensor, etc. The stimulator analyzes the sensor output to determine the corresponding stimulation rate.

A variety of signal processing techniques have been used to process the raw activity sensor output. In one approach, the raw signals are rectified and filtered. Also, the frequency of the highest signal peaks can be monitored. Typically, the end result is a digital signal indicative of the level of sensed activity at a given time. The activity level is then applied to a transfer function that defines the pacing rate (also known as the sensor indicated rate) for each possible activity level. Attention is drawn to U.S. Pat. No. 5,074,302 to Poore, et al., entitled "Self-Adjusting Rate-Responsive Pacemaker and Method Thereof", issued Dec. 24, 1991. This patent has a controller that relates the patient activity level signal to a corresponding stimulation rate. In addition, the controller uses the activity signal over a long time period to determine the adjustment of the corresponding stimulation rates. The activity signal can also indicate when a patient is sleeping to modify the pacing rate as set forth in U.S. Pat. No. 5,476,483 to Bornzin, et al, entitled "System and Method for Modulating the Base Rate during Sleep for a Rate-Responsive Cardiac Pacemaker", issued Dec. 19, 1995, which is hereby incorporated by reference in its entirety.

Another method of determining the stimulation rate based upon metabolic need is based upon the body position of a patient. Studies have shown that that a patient being upright indicates a higher stimulation rate than for a patient lying down. An example is U.S. Pat. No. 5,354,317 to Alt, entitled "Apparatus and Method of Cardiac Pacing Responsive to Patient Position", issued Oct. 11, 1994. In this patent, the controller monitors a motion sensor to produce a static output which represents the position of the patient, i.e., lying down or upright. This static output is used to determine whether a sleep indicated rate or an awake base rate should be used. However, this system is completely dependent upon the proper orientation of the stimulator housing during implantation for consistent and reliable results.

To further improve the stimulator's ability to mimic the heart's natural rhythm, a combination of monitoring both the patient's activity level and the body position has been envisioned. U.S. Pat. No. 5,593,431 to Sheldon, entitled "Medical Service Employing Multiple DC Accelerometers for Patient Activity and Posture Sensing and Method", issued Jan. 14, 1997, sets forth a system which monitors both parameters. This patent sets forth a cardiac stimulator which uses a multi-axis DC accelerometer system to monitor both patient position and patient activity. Unfortunately, this accelerometer also depends upon a known orientation during implant and repeated postoperative calibrations for proper operation due to shifting of the stimulator within the implant pocket.

The ability to accurately determine both the patient's activity level and the patient's body posture would greatly benefit many patients by providing a more metabolically correct stimulation rate. As well, this combination of sensors could be used to determine the accuracy of other sensors such as PDI, $O_2$ saturation, etc. This enables the controller of the stimulator to blend the outputs of the various sensors to provide the benefit of the each individual sensor. Also, in the case of implantable cardioverter/defibrillators (ICDs), these two outputs would allow modification of the defibrillator thresholds based upon time of day and posture of the patient.

Accordingly, it would be desirable to develop an implantable cardiac stimulator which adjusts the stimulation level based upon the patient activity and the patient body position via sensors that are not device implant orientation sensitive.

SUMMARY OF THE INVENTION

The present invention is directed towards an implantable cardiac stimulation device which determines cardiac stimulation levels based upon the patient's current body position and activity level while eliminating special implantation or calibration procedures. To determine the body position and the activity level, the stimulator monitors the output of a multi-axis DC accelerometer or a combination of sensors to include oxygen saturation, PDI, minute ventilation sensors, etc.

To determine the patient's current body position, the controller establishes the output of at least two DC accelerometers during times of high activity as the patient's standing position. Lower activity levels associated with the other body orientations while lying down are also deduced in a similar manner. Then, the stimulator correlates the current outputs of the DC accelerometers with the standing position to determine the current body position and uses the previous and current body positions and the activity level (preferably calculated from the AC acceleration in the anterior-posterior axis, the axis which has the best correlation with the patient activity), to determine the instantaneous stimulation needed.

Because this stimulator depends upon the combination of activity signals and position signals from the multi-axis accelerometer, this device is not dependent upon a predetermined implant orientation or repeated calibration of the accelerometer after implant. If the device should shift within the patient after implant, the controller will accommodate this change during the patient's next high activity period.

As such, this device monitors the activity and position signals from the multi-axis accelerometer to determine the indicated activity level of the patient and the current body position and then determines the type and intensity of cardiac stimulation the patient needs.

In a further aspect of a preferred embodiment of the present invention, the calculated standing position is monitored to detect changes that may indicate the presence of twiddler's syndrome.

BRIEF DESCRIPTION OF THE DRAWINGS

The above and other aspects, features, and advantages of the present invention will be more apparent from the following more particular description thereof, presented in conjunction with the following drawings wherein:

FIGS. 5A–5B set forth a flow chart for a method for determining the current position of the patient in accordance with the present invention;

DETAILED DESCRIPTION OF THE INVENTION

Figure 1:
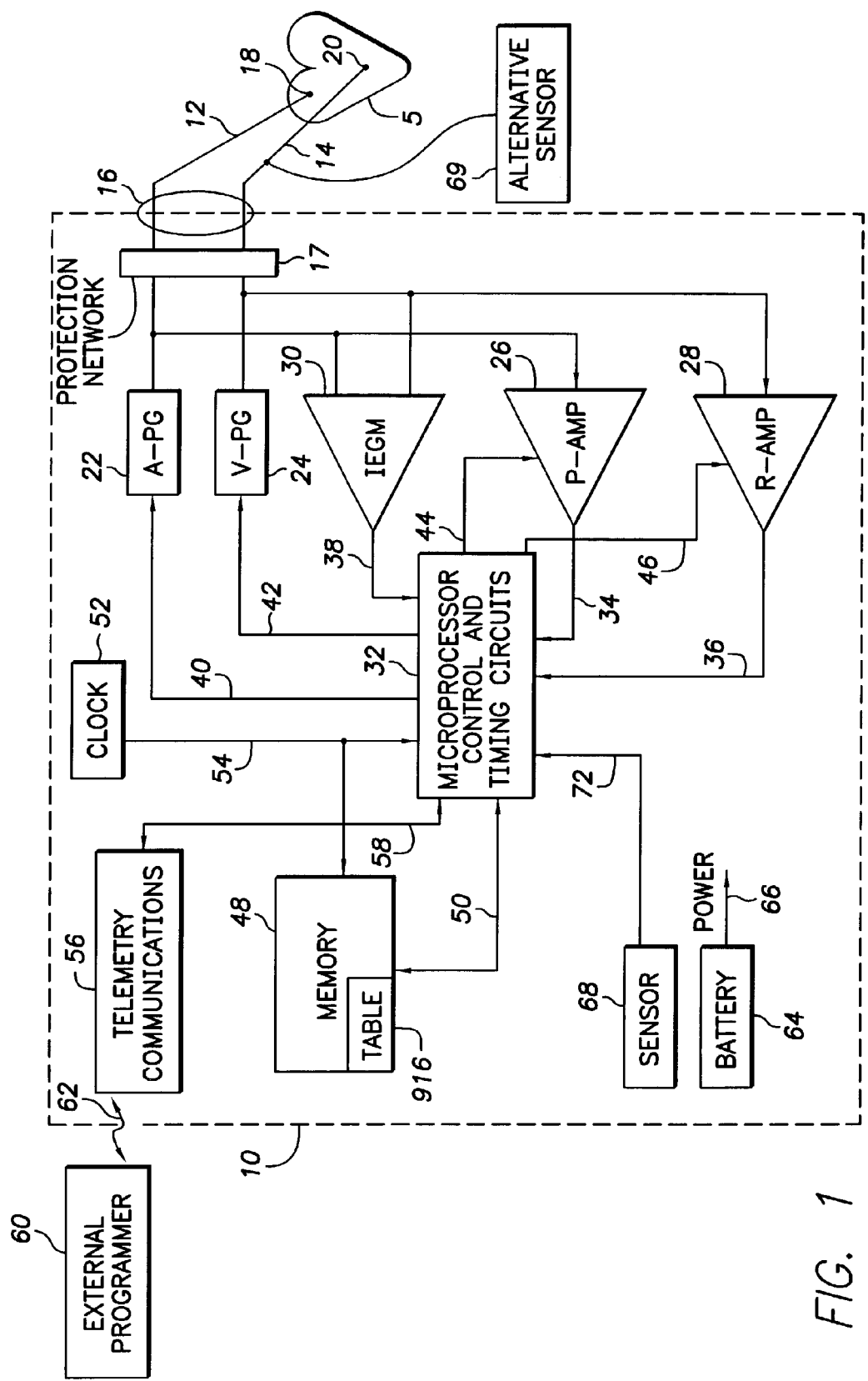
FIG. 1 is a block diagram of an implantable stimulation device as set forth in the present invention.

Referring now to FIG. 1, an implantable cardiac stimulation device in accordance with the present invention is shown as a dual sensor rate responsive pacemaker 10. It is well within the scope of this invention to operate this stimulation device in a demand mode as is well known within the art. Also, the principles of this invention would be easily applied to defibrillation theory by one of ordinary skill in the art. While the preferred embodiment is directed towards a stimulation device which uses a multi-axis (two or more axis) accelerometer for determining the pacing rate and stimulation intensity, it is well within the scope of this invention to apply the principles of this invention for use with other physiologic sensors that also indicate patient position and activity.

FIG. 1 sets forth a simplified block diagram of the stimulation device 10. The stimulation device 10 is coupled to a heart 5 by way of two leads 12, 14. The first lead 12 has at least one electrode 18 in contact with the atrium of the heart 5, and the second lead has at least one electrode 20 in contact with the ventricle of the heart 5. The leads 12, 14 are electrically and physically connected to the stimulation device 10 through a connector 16 which forms an integral part of the housing (not shown) in which the circuits of the stimulation device 10 are housed. The connector 16 electrically protects circuits within the stimulation device 10 via protection network 17 from excessive shocks or voltages that could appear on electrodes 18, 20 in the event of contact with a high voltage signal, e.g., from a defibrillator shock.

The leads 12, 14 carry the stimulating pulses to the electrodes 18, 20 from the atrial pulse generator (A-PG) 22 and a ventricular pulse generator (V-PG) 24, respectively. Further, the electrical signals from the atrium are carried from the electrode 18 through the lead 12 to the input terminal of the atrial channel sense amplifier (P-AMP) 26. The electrical signals from the ventricle are carried from the electrode 20 through the lead 14 to the input terminal of the ventricular channel sense amplifier (R-AMP) 28. Similarly, electrical signals from both the atrium and the ventricle are applied to the inputs of the IEGM (intracardiac electrogram) amplifier 30. The stimulation device 10 detects an evoked response from the heart to an applied stimulus, allowing the detection of the capture with a suitable broad bandpass filter. The IEGM amplifier 30 is also used during the transmission to an external programmer 60.

The stimulation device 10 uses a controller (microprocessor control and timing circuits) 32 that typically includes a microprocessor to carry out the control and timing functions. The controller 32 receives output signals from the atrial amplifier 26, the ventricular amplifier 28, and the IEGM amplifier 30 over the signal lines 34, 36, 38, respectively. The controller 32 then generates trigger signals that are sent to the atrial pulse generator 22 and the ventricular pulse generator 24 over the signal lines 40, 42, respectively.

The stimulation device 10 also includes a memory 48 that is coupled to the controller 32 over a suitable data/address bus 50. This memory 48 stores customized control parameters for the stimulation device's operation for each individual patient. Further, the data sensed by the IEGM amplifier 30 may be stored in the memory 48 for later retrieval and analysis.

A clock circuit 52 directs appropriate clock signal(s) to the controller 32 as well as any other circuits throughout the stimulation device 10, e.g., to the memory 48 by a clock bus 54.

The stimulation device 10 also has a telemetry communications circuit 56 which is connected to the controller 32 by way of a suitable command/data bus 58. In turn, the telemetry communications circuit 56 is selectively coupled to the external programmer 60 by an appropriate communications link 62, such as an electromagnetic link. Through the external programmer 60 and the communications link 62, desired commands may be sent to the controller 32. Other data measured within or by the stimulation device 10 such as IEGM data, etc., may be sorted and uploaded to the external programmer 60.

The stimulation device 10 derives its electrical power from a battery 64 (or other appropriate power source) which provides all operating power to all the circuits of the stimulation device 10 via a POWER signal line 66.

The stimulation device 10 also includes a sensor 68 that is connected to the controller 32 over a suitable connection line 72. In the preferred embodiment, this sensor detects patient activity and indicates the patient's position via a multi-axis (i.e., two or more axis) DC accelerometer. However, any appropriate sensor or combination of sensors which indicate levels of patient activity and indicate the patient's position could be used. Other such sensors, such as a minute ventilation sensor, blood pressure sensor, PDI sensor, etc., can be used to in lieu of or supplemental to the activity signal from the accelerometer. In the case of some of these alternative sensors, the sensor could be placed on the lead 14 as shown by an alternative sensor 69.

The above described stimulation device 10 generally operates in a conventional manner to provide pacing pulses at a rate that comfortably meets the patient's metabolic demands. In a typical case, the controller 32 uses the signals generated by the sensor 68 (or other alternative sensors 69) to determine both the activity level and the body position of the patient, both indicators of metabolic need. Many methods of determining the activity level of the patient are well known within the art. Attention is drawn to the '483 patent, which is hereby incorporated by reference. To regulate the pacing rate, the controller 32 provides a trigger signal to the atrial pulse generator 22 and/or the ventricular pulse generator 24. The timing of this signal (to a large extent) is determined by the activity level of the patient, body position, and the individualized control parameters.

Figure 2:
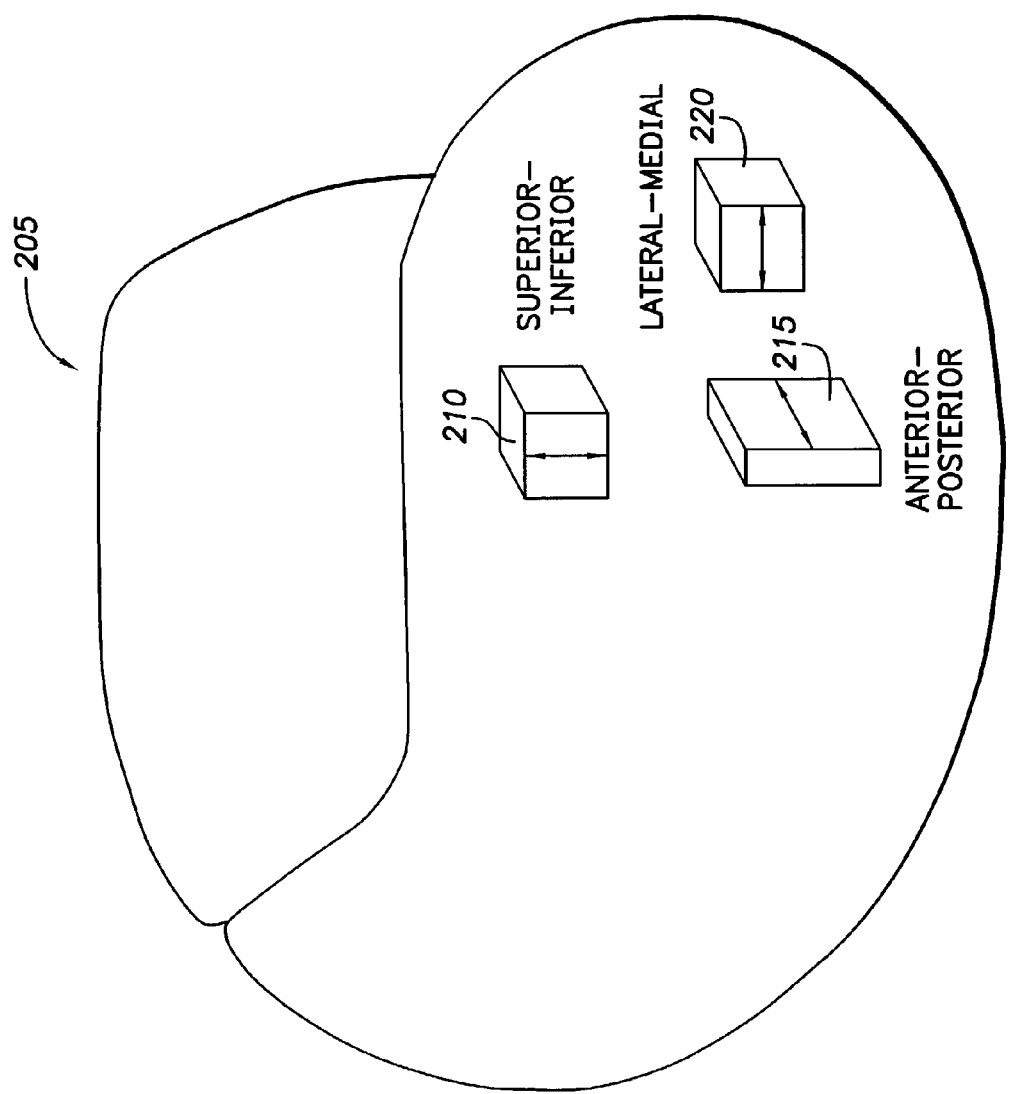
FIG. 2 is an example of an exemplary three-axis accelerometer within a stimulator housing, suitable for use with the present invention.

In embodiments of the present invention, each multi-axis DC accelerometer consists of at least two DC accelerometers (hereafter known as DC sensors), preferably mounted essentially orthogonal to each other. FIG. 2 sets forth an exemplary embodiment with three DC sensors attached to the inside of a stimulator housing 205. In the example of FIG. 2, these three DC sensors are labeled superior-inferior 210, anterior-posterior 215, and lateral-medial 220, respectively. Each DC sensor can also generate the activity level of the patient, i.e., AC acceleration.

Each of the DC sensors 210, 215, 220 is preferably a surface micromachined integrated circuit with signal conditioning as is well known in the art. Employing surface micromachining, a set of movable capacitor plates are formed extending in a pattern from a shaped polysilicon proof mass suspended by tethers with respect to a further set of fixed polysilicon capacitor plates. The proof mass has a sensitive axis along which a force between 0 G and +50 G effects the physical movement of the proof mass and a change in the measured capacitance between the fixed and moveable plates. The measured capacitance is transformed by the on-chip signal conditioning circuits into a low voltage signal. Further information regarding the physical construction of the DC sensors can be found in the '431 patent, hereby incorporated by reference in its entirety. However, many other types of accelerometers are commercially available, and it would be obvious to one of ordinary skill in the art to use other types of accelerometers in place of the above described multi-axis DC accelerometer. While, three or more DC sensors are preferred, systems of the present invention can be formed from two DC sensors, as described further below.

To determine both the activity level and the body position of the patient, the controller 32 monitors the output of each of the DC sensors. Preferably using standard analog to digital conversion techniques, the output of each of the DC sensors is filtered to separate an AC signal component (representing the activity level) and a DC signal component (representing the body position). Then, the two resultant signals are further processed to determine two corresponding digital outputs which represent the instantaneous signal level of each signal. The resulting activity digital signals are then further processed to determine the activity level of the patient by methods well known within the art. One example is contained in the '302 patent, hereby incorporated by reference in its entirety. The resulting two position signals are processed to determine the indicated body position as discussed below.

Knowing the activity level, the activity variance measurements can be determined. Activity variance is the long term variance in the patient's activity as derived by the controller 32 and gives a further indication of the patient's activity. For example, a high variance measurement indicates the patient has been quite active and a low variance measurement indicates that a patient has been resting or sleeping. Preferably, these activity and activity variance signals are calculated from the accelerometer output in the anterior-posterior axis which has the best correlation with the patient physical activity. For further information regarding the determination of the activity variance, attention is drawn to the '483 patent, hereby incorporated by reference in its entirety.

Figure 3:
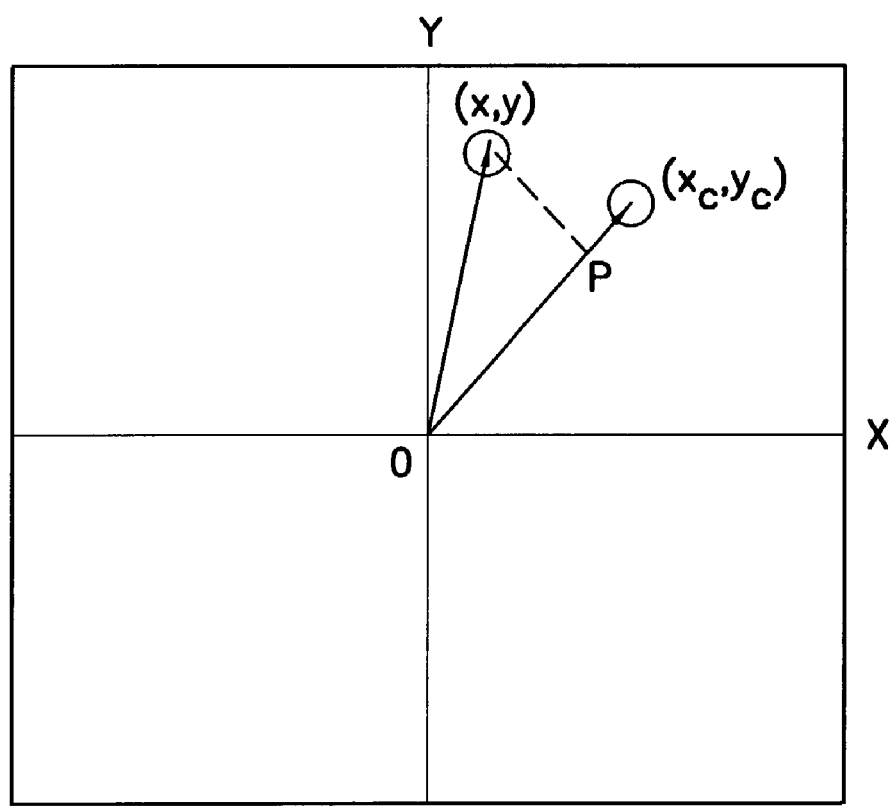
FIG. 3 sets forth a two-dimensional cluster plot as outputted by the accelerometer.

Once the activity level of the patient is determined, the controller 32 then determines the instantaneous position of the stimulator housing 205 within the patient. By using the digital outputs of the lateral-medial 220 and superior-inferior 210 DC sensors shown in FIG. 2, a two dimensional plot can be created to show the clusters in the different graph positions which represent different body postures of the patient. When the stimulator housing 205 shifts within the patient's body, the clusters on the two dimensional plot will rotate correspondingly, but the relative positions of the clusters will not change. The graph of FIG. 3 is defined as follows: x is the current indicated position in the lateral-medial axis, y is the current indicated position in the superior-inferior axis, and ($x_c$, $y_c$) represents the average of the digital outputs that have correlated to the patient being oriented in a standing position.

Figure 4:
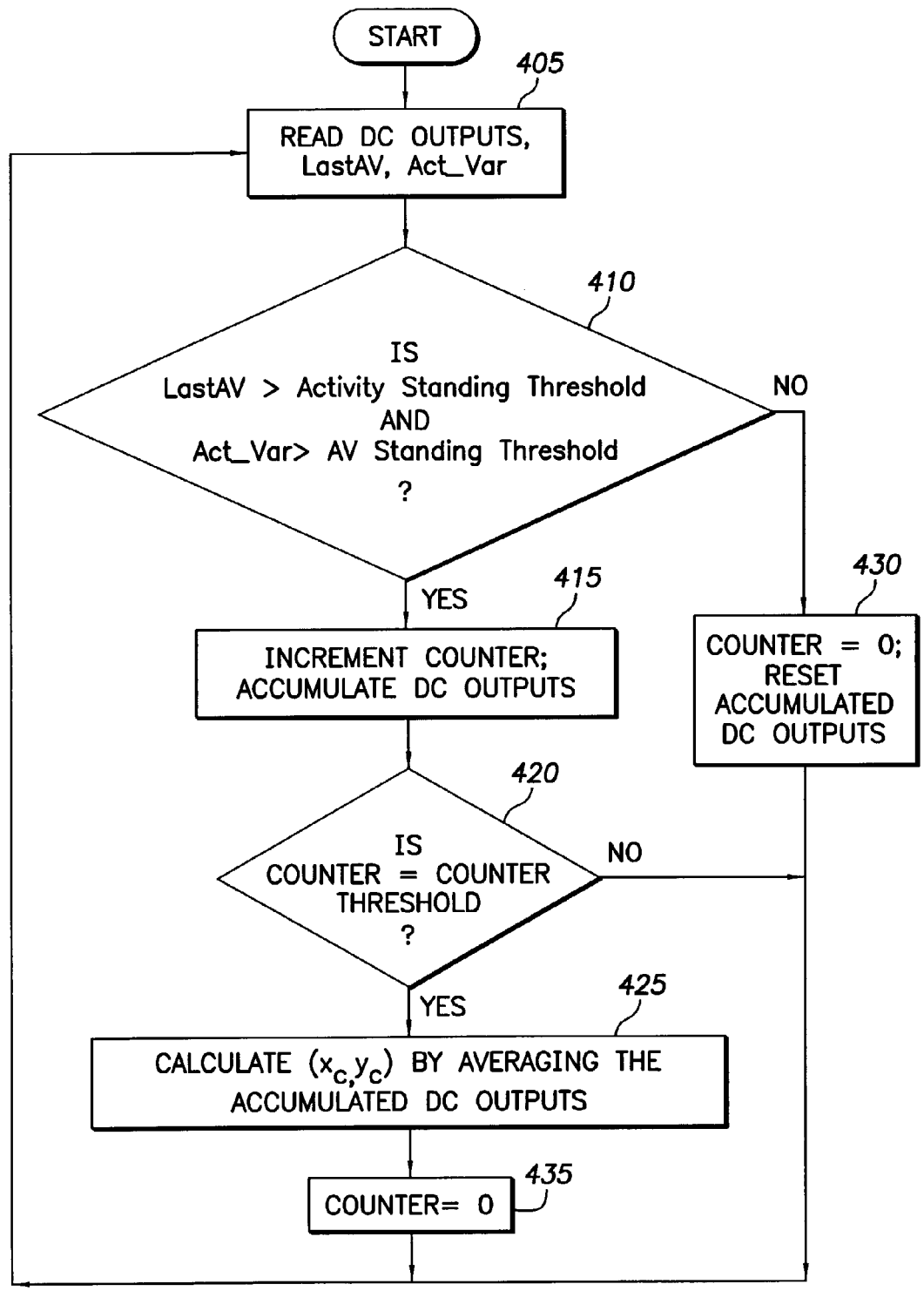
FIG. 4 sets forth a flow chart for a method of determining the variables ($x_c$, $y_c$) in accordance with the present invention.

To determine the orientation of the accelerometer indicating that the patient is standing, attention is drawn to FIG. 4 which shows an exemplary flowchart. First, at step 405, the activity level (LastAV) and the activity variance (Act_Var) measurements are monitored as well as the current digital outputs from the DC sensors, e.g., 210, 220. The digital outputs are used to determine an initial (x, y) value. Then, at step 410, both the activity level (LastAV) and the activity variance (Act_Var) measurements are compared to corresponding standing thresholds, respectively Activity Standing Threshold and AV Standing Threshold.

If both variables are above their corresponding standing thresholds, the controller 32 continues to step 415, where the controller 32 increments a counter and adds the current digital outputs indicative of (x, y) to an accumulated (x, y) value. Then, at step 420, the controller 32 determines if the counter has reached its threshold value (e.g., 120 counts).

If the controller 32 has not reached its threshold value, the controller 32 returns to step 405. If the controller 32 has reached its threshold value, the controller 32 continues to step 425 where the controller 32 determines ($x_c$, $y_c$) by averaging the accumulated (x, y) value over the counter period. Afterwards, in step 435, the controller 32 resets the counter to zero to prepare for another update. The controller then returns to step 405.

As shown in step 430, if one of these variables is not above the corresponding standing threshold, then the counter and the accumulated (x, y) values are reset to 0, and the controller 32 returns to step 405.

Once the controller 32 has determined what position ($x_c$, $y_c$) corresponds to the patient standing, the controller 32 then determines the current body position. FIGS. 5A–5B sets forth an exemplary flow chart to determine the current body position of the patient. To begin the process, the controller 32 sets the current position code (Current Position) equal to 1. The current position code is a binary code of 1 or 0 which indicates whether the patient is standing (1) or lying down (0). Additionally, the controller 32 sets the time the patient has been at rest, $T_{REST}$, equal to 0, and stores $T_{REST}$ into memory 48 at step 501. At step 505, the controller 32 reads the current position code and the activity level (LastAV) out of the memory 48. The activity level (LastAV) is determined from the digital output of the AC portion of the DC sensor output as discussed above. The controller 32 then determines the projection value (P).

The projection value (P) is a numerical indication of the correlation between the current body position (x, y) to the determined standing position ($x_c$, $y_c$) as calculated below:

$$P = \frac{(x^* x_c + y^* y_c)}{(x_c^2 + y_c^2)}$$

If the projection value (P) indicates a correlation value of greater than a standing threshold, e.g., at least 0.65, the current body position (x, y) is considered to be standing. For example, using the values referenced in the discussion of FIG. 3, a projection value (P) of 0.968 is calculated. Accordingly, the current (x, y) value shown in the example of FIG. 3 would be considered to correspond to the patient being in a standing position.

Once the controller 32 has determined these three values (i.e., $T_{REST}$, activity level (LastAV), and the projection value (P)), it proceeds to step 510. At step 510, the controller 32 determines if the current position code indicates that the patient was standing. If the current position code 1, the controller 32 proceeds to step 515.

Then, at step 515, the controller 32 determines if the current projection value (P) is less than a standing threshold (Standing_Threshold), e.g., 0.65, and if the activity level (LastAV) is below an activity threshold (Act_Avg). If either of these conditions is not true at step 515, the controller 32 proceeds to step 520 where the controller 32 stores the current position code as the last position code (Last Position) and sets the current position code equal to 1, indicating that the patient is still standing. The controller 32 then returns to step 505.

If both of these conditions are true at step 515, the controller 32 proceeds to step 525 where the controller 32 compares the current value of $T_{REST}$ with a resting threshold (Rest_Enough). If $T_{REST}$ is not equal to a resting threshold (Rest_Enough), then $T_{REST}$ is incremented at step 530. At step 535, the controller 32 stores the current position code as the last position code and sets the current position code equal to 1, indicating that the patient is standing since the patient has not been at rest for a sufficient period of time. The controller 32 then returns to step 505.

If $T_{REST}$ is equal to the resting threshold at step 525, then, at step 540, the last position code is set equal to the current position code and the current position code is set to 0, indicating that the patient is no longer standing. Then, the controller 32 returns to step 505.

Returning to step 510, if the current position code was not equal to 1, the controller 32 proceeds to step 545, where the controller 32 determines if the projection value (P) is greater than the standing threshold (e.g., 0.65) and if the activity level (LastAV) is greater than the activity threshold (Act_Avg), e.g., indicating that the patient is exercising. If these conditions are both true at step 545, the controller 32 proceeds to step 550 where $T_{REST}$ is set to 0. The controller 32 then proceeds to step 555 where the last position code is set equal to the current position code and the current position code is set to 1 to indicate that the patient is now standing. The controller 32 then returns to step 505.

If either condition is not met at step 545, then the controller 32 proceeds to step 560 where the last position code is set equal to the current position code and the current position code is set to 0 to indicate that the patient is still at rest. The controller 32 then returns to step 505.

While a two dimensional calculation has been described, one of ordinary skill would appreciate that this calculation could be expanded to a three dimensional case with the use of three DC sensors, e.g., 220, 210, 215 of FIG. 2, respectively indicating the (x, y, z) positions of the patient's body. In such a case the projection value (P) would be calculated as:

$$P = \frac{(x^* x_c + y^* y_c + z^* z_c)}{(x_c^2 + y_c^2 + z_c^2)}$$

One application of this method of determining body position is in orthostatic compensation pacing. Patients who suffer from long term diabetes tend to develop neuropathy from the long term exposure of their nerves to excessive blood sugar levels. This condition erodes the body's ability to adequately control the heart rate. In particular, this condition renders the patient unable to compensate for the dramatic drop in blood pressure upon standing after sitting or lying down for an extended period of time due to an inability of the body to increase the heart rate and constrict the system resistance and capacitance of its blood vessels.

To overcome this condition, the controller 32 compensates for the change in the patient position by triggering an orthostatic compensation rate when the body position, the activity level signal, and the activity variance indicate a sudden change in the patient's activity after a prolonged period of inactivity. This pacing regime is blended into a traditional transfer function indicated by the activity level and activity variance measurements as discussed below.

Figure 6:
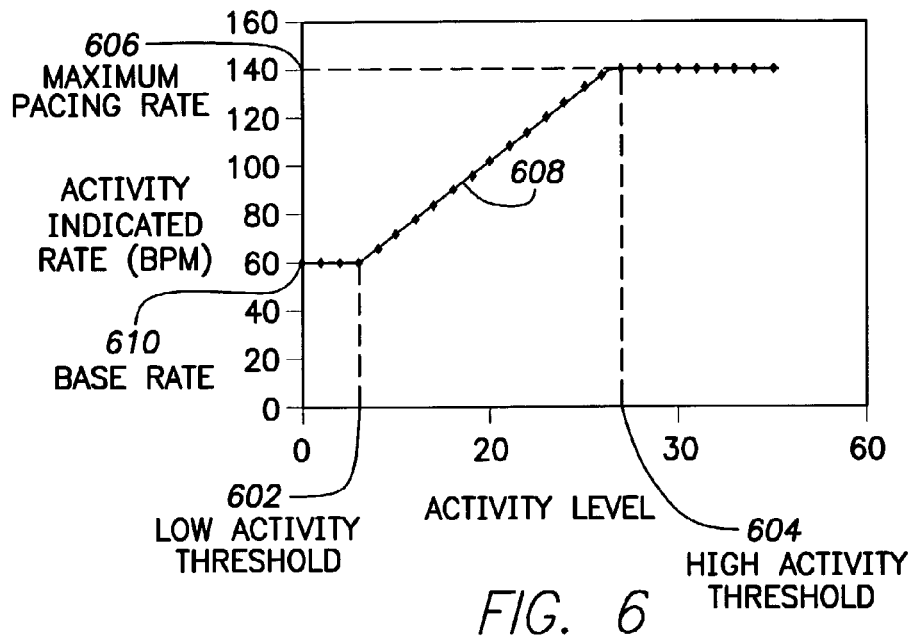
FIG. 6 sets forth a transfer function for determining the activity indicated rate.

In FIG. 6, the activity indicated rate (AIR) is illustrated. The transfer function is used by the controller 32 to correlate the activity level measurements shown along the horizontal axis to the activity indicated pacing rates shown along the vertical axis. The controller 32 then triggers the appropriate pulse generator 22, 24 at the activity indicated rate. It should be noted that an appropriate transfer function can be used based upon individual need. In addition, different modes of pacing (e.g., DDD, VVI, etc.) can be accommodated by this method.

Two activity levels are noted on the horizontal axis of the transfer function: a low activity threshold 602 and a high activity threshold 604. For activity level measurements above the high activity threshold 604, the pacing rate is maintained at a maximum pacing rate 606 as determined by the physician. For activity level measurements between the low activity threshold 602 and the high activity threshold 606, the activity indicated pacing rate varies according to a programmed transfer function 608. In this case, the activity indicated pacing rate varies linearly between a base rate 610 and a maximum pacing rate 606. However, this transition can be programmed to meet the patient's need by the physician in many different ways as is well known in the art or periodically adjusted by the controller 32 as set forth in U.S. Pat. No. 5,514,162 to Bornzin, et al., entitled "System and Method for Automatically Determining the Slope of a Transfer Function for a Rate-Responsive Cardiac Pacemaker", issued May 7, 1996, hereby incorporated by reference.

Figure 7:
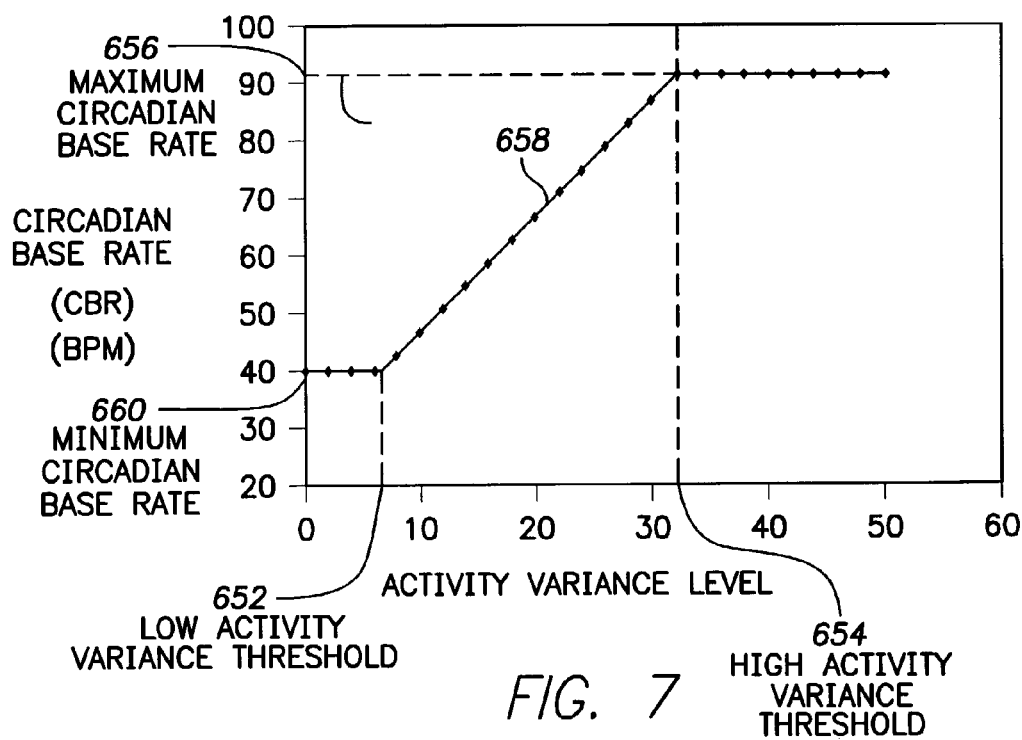
FIG. 7 sets forth a transfer function for determining the circadian base rate.

The circadian base rate (CBR), illustrated in FIG. 7, is established by monitoring the activity variance measurements (also known as the long term variance in activity) as described more fully in the '483 patent, hereby incorporated by reference in its entirety. The transfer function is used by the control system to correlate the activity variance level shown along the horizontal axis to the CBR shown along the vertical axis. The controller 32 then triggers the appropriate pulse generator 22, 24 at the activity indicated rate. Preferably, an appropriate transfer function can be used based upon individual need. In addition, different modes of pacing, i.e., DDD, VVI, etc.) can be accommodated by this method.

Two activity variance levels are noted on the horizontal axis of the transfer function: a low activity variance threshold 652 and a high activity variance threshold 654. For activity variance level measurements above the high activity variance threshold 654, the CBR is maintained at a maximum pacing rate 656 as determined by the physician. For activity level measurements between the low activity variance threshold 652 and the high activity variance threshold 654, the CBR varies according to a programmed transfer function 658. In this case, the CBR varies linearly between a minimum CBR 660 and a maximum CBR 656. For activity variance level measurements below the low activity variance threshold 652, the controller 32 sets the CBR as defined by the minimum CBR 660.

A patient's activity level is monitored and activity variance measurements are calculated to determine when and how long a patient typically rests or sleeps. These two terms define a stimulation rate which is below the programmed base rate such that the controller 32 triggers pacing pulses at a lower pacing rate during sleep. This lower pacing rate more closely mimics the natural cardiac rhythm exhibited during rest or sleep.

Figure 8:
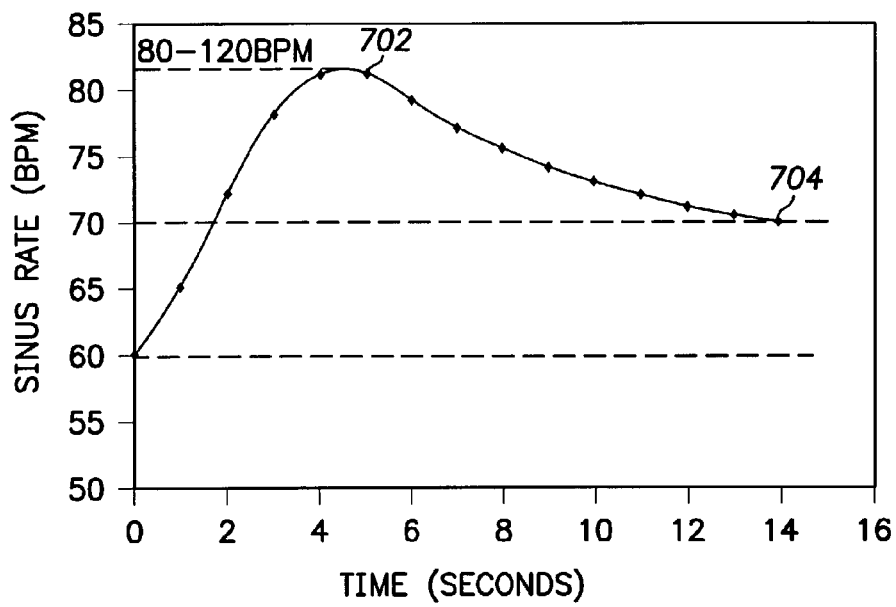
FIG. 8 sets forth a normal heart rate response when a patient stands after a prolonged period of lying down.

FIG. 8 sets forth one sample of an experimentally observed orthostatic response of a normal healthy person. Upon standing after a prolonged period of sitting or lying down, the normal sinus rate quickly increases to a peak 702 of approximately 80 to 120 bpm within 10 seconds. Then, the rate slowly decreases to the base rate, typically 70 bpm, in about 10 to 20 seconds.

Figure 9:
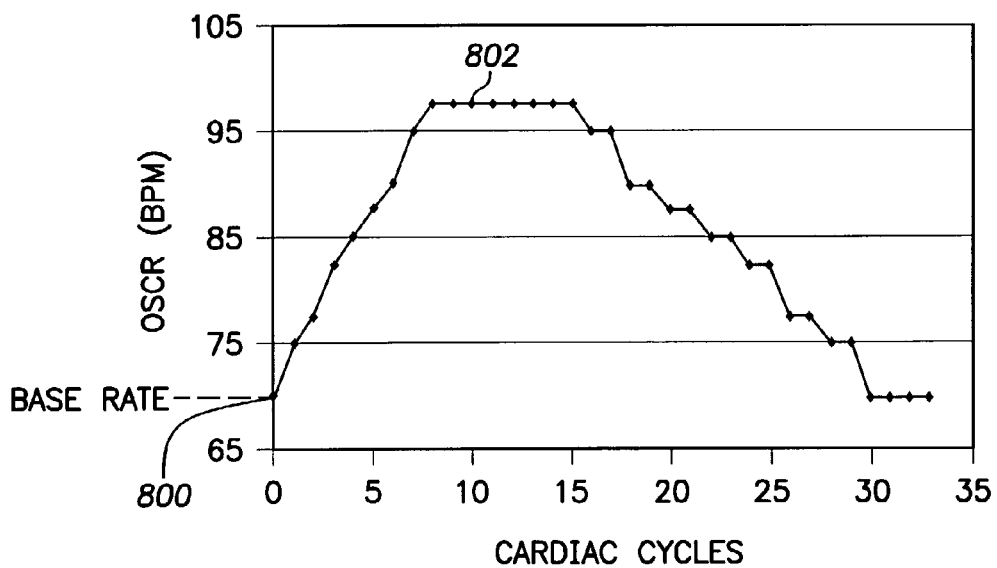
FIG. 9 sets forth a time table of an example of an orthostatic compensation stimulation regime.

FIG. 9 shows an exemplary orthostatic compensation pacing regime that can be delivered to the pacemaker patient upon the detection of a posture change from standing up to lying down. The controller 32 increases the orthostatic compensation rate (OSCR) from a base rate 800 to a peak 802 in seven cardiac cycles. After the OSCR reaches the maximum, it is maintained at the maximum level for another 7 cardiac cycles. The rate then slowly decreases down to the base rate in about 12 cardiac cycles. Preferably, the specific orthostatic compensation pacing regime, including the maximum OSCR, the slopes and the duration, can be varied and is typically determined by the physician. As such, the regime set forth in FIG. 9 is only an example.

Figure 10:
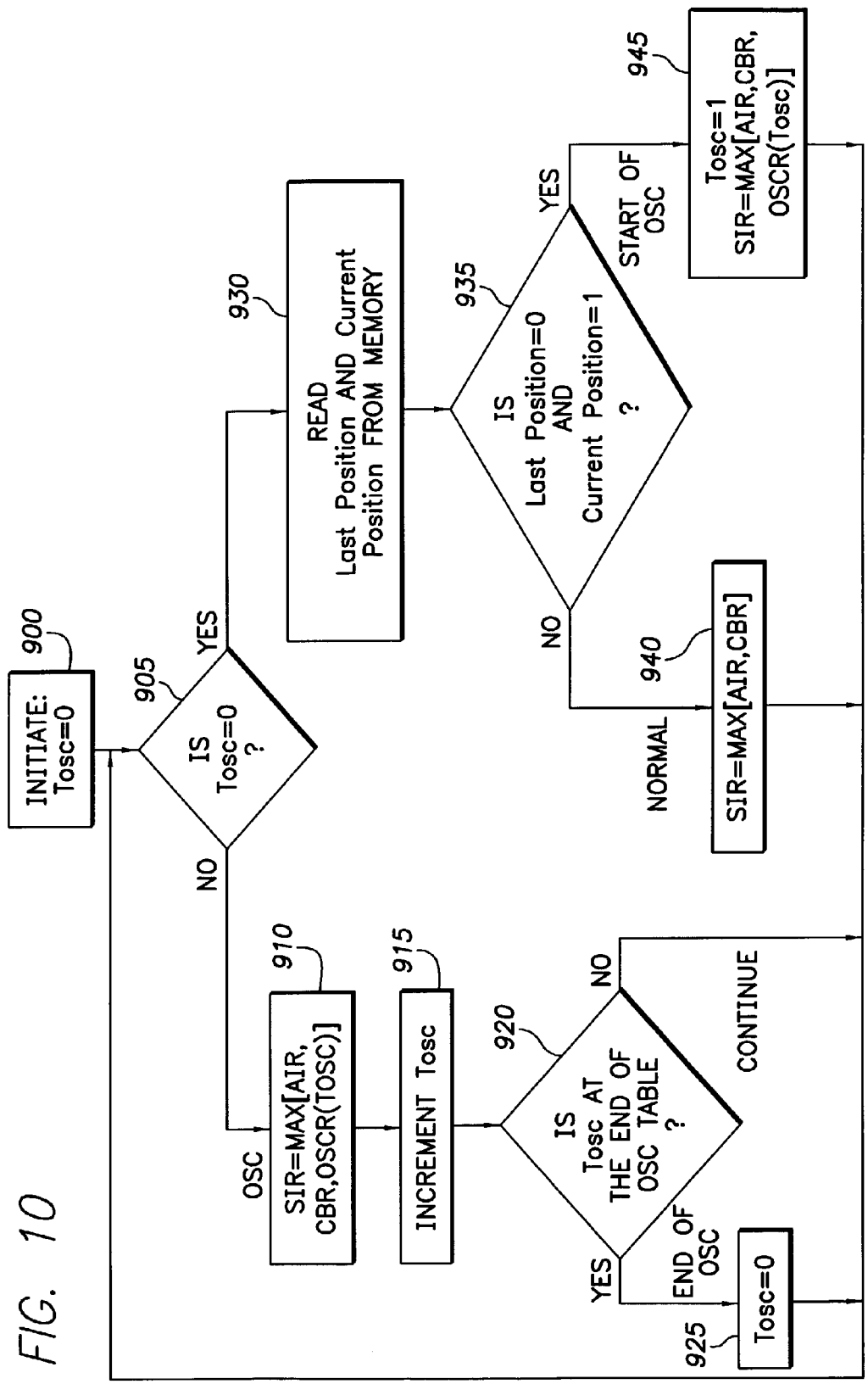
FIG. 10 sets forth a flow chart for a method of determining an instantaneous stimulation rate in accordance with the present invention.

FIG. 10 sets forth an exemplary flow chart describing how the controller 32 determines the immediate pacing rate. Upon initiation at step 900, the controller 32 sets the value of the $T_{OSC}$ counter equal to 0. The $T_{OSC}$ counter represents the cycle pointer of the orthostatic compensation pacing regime as set forth on the x-axis of FIG. 9. The controller 32 then proceeds to step 905 where the controller 32 determines if the $T_{OSC}$ counter is equal to 0. If this condition is not true at step 905, then the controller 32 is already within the orthostatic compensation (OSC) pacing regime and proceeds to step 910. The controller 32 then sets the stimulation rate (SIR) to be the maximum of an activity indicated rate (AIR), a circadian base rate (CBR), or an orthostatic compensation rate (OSCR($T_{OSC}$)). Preferably, this function OSCR($T_{OSC}$) is performed as a look-up function of data within an orthostatic compensation table 916 within the memory 48. The controller 32 then proceeds to step 915, where the controller 32 increments the $T_{OSC}$ counter.

If at step 920, the $T_{OSC}$ counter has reached the end of the orthostatic compensation table 916, the controller 32 resets the $T_{OSC}$ counter to 0 at step 925 because the orthostatic compensation regime has been completed. The controller 32 then returns to step 905 to continue the orthostatic compensation regime. If at step 920, the $T_{OSC}$ counter has not reached the end of the orthostatic compensation table, then the controller 32 proceeds directly to step 905.

Returning to step 905, if the $T_{OSC}$ counter is equal to 0, the controller 32 proceeds to step 930. This condition represents that the patient is not currently receiving the orthostatic compensation regime. The controller 32 then reads the last position and the current position codes from the memory 48. The controller 32 then, at step 935, determines if the last position code is equal to 0 and if the current position code is equal to 1. If these conditions are not met at step 930, then, at step 940, the controller 32 sets the stimulation rate (SIR) to the maximum of the activity indicated rate (AIR) and the circadian base rate (CBR) as discussed above. If these conditions are met at step 935, then the patient has just stood up after a period of lying down. In this case, the controller 32 triggers the orthostatic compensation regime. To this end, the controller 32 proceeds to step 945 where the controller 32 sets the $T_{OSC}$ counter to 1 and sets the stimulation rate (SIR) to be equal to the maximum of the activity indicated rate (AIR), the circadian base rate (CBR), and the orthostatic compensation rate (OSCR($T_{OSC}$)) as set forth above. The controller 32 then returns to step 905 where the orthostatic compensation routine will continue through step 910 as previously described.

Once the controller 32 determines the instantaneous stimulation rate (SIR), the controller 32 returns to the posture detection mode (see FIGS. 4 and 5) to determine the new current patient position. Once the controller 32 updates the last position code with the current position code and determines the current patient position, the controller 32 then returns to update the instantaneous stimulation rate (SIR). Also, any time the controller 32 detects that the activity level exceeds the standing threshold, the controller 32 returns to update the standing center ($x_c$, $y_c$) Other applications of this invention include adjustment of stimulation parameters such as the AV delay, the PVARP, the stimulation level, and timing. For example, the AV delay could be shortened when the patient is known to be standing. Also, the base rate can be adjusted for a patient being in a standing position versus lying down.

Also, knowing the position and the activity level of the patient can allow the triggering of monitoring functions under known conditions. For instance, when a patient is reliably known to be sleeping (i.e., inactive and lying down), monitoring functions such as heart sounds, respirations, intrinsic heart sounds, etc., can be measured for long-term monitoring of cardiovascular function.

Figure 11:
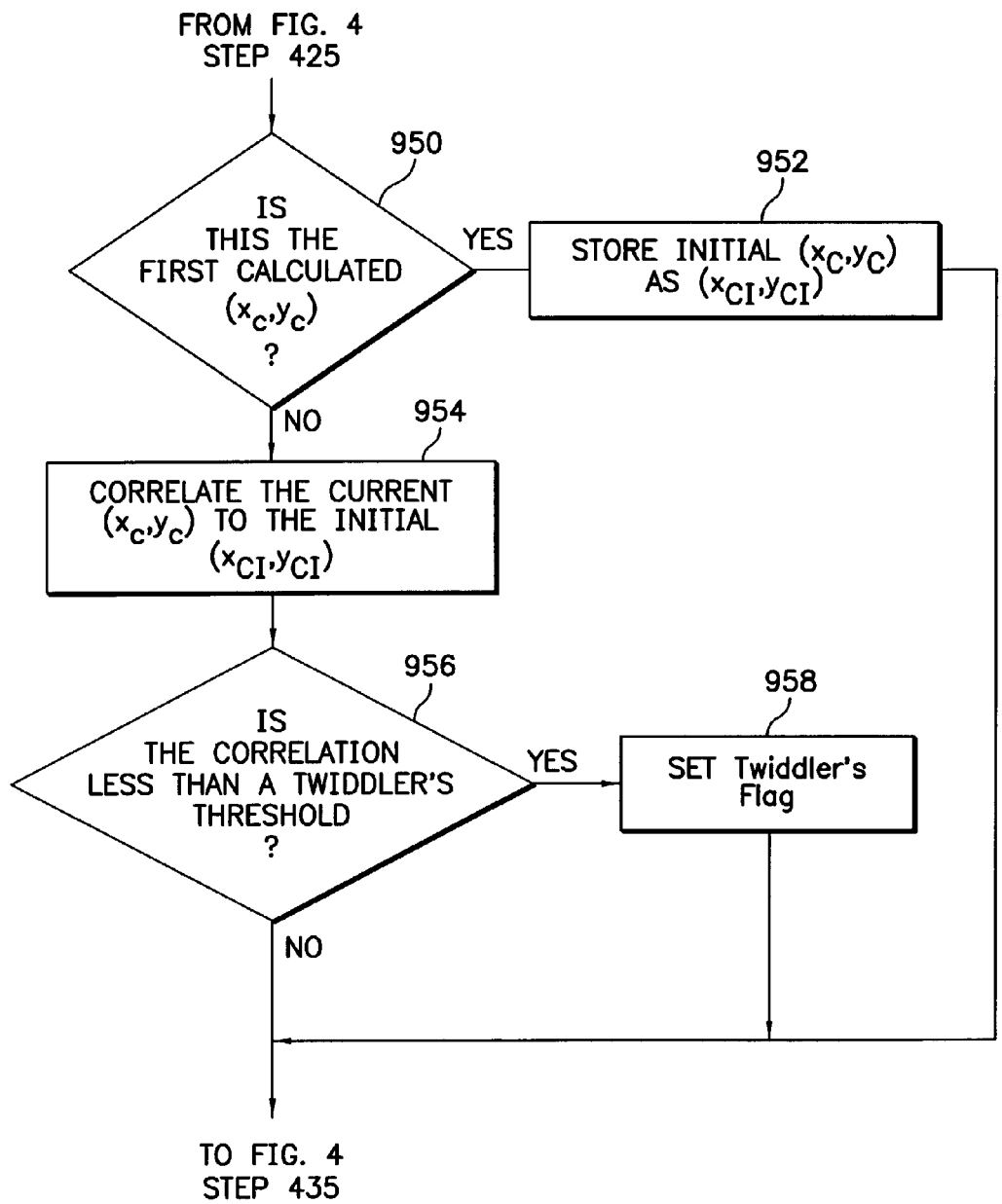
FIG. 11 set forth a flow chart of an exemplary supplement to the flow chart of FIG. 4 for detecting twiddler's syndrome.

As an additional feature, embodiments of the present invention may include the capability to detect twiddler's syndrome. Twiddler's syndrome refers to the condition where an implanted cardiac stimulation device sits loosely in the pocket in the patient's chest. Consequently, the cardiac stimulation device may rotate in the pocket due to purposeful or inadvertent activity by the patient, eventually causing lead dislodgment or fracture. By comparing the currently calculated standing position ($x_c$, $y_c$) to an initial calculation of the standing position (i.e., its implantation position ($x_{ci}$, $y_{ci}$)), embodiments of the present invention can recognize movements of the cardiac stimulation device that may correspond to twiddler's syndrome. FIG. 11 shows a flow chart of an exemplary supplement to the flow chart of FIG. 4 that may be used for detecting twiddler's syndrome. This supplement is placed following block 425 of FIG. 4 where the current standing position value ($x_c$, $y_c$) is calculated. In step 950, it is determined whether this is the first calculation of ($x_c$, $y_c$). If this is the first calculation, an initial, e.g., an implantation, standing position value ($x_{ci}$, $y_{ci}$) is stored in memory 48 and the process continues in step 435. Following subsequent calculations of the standing position, the process continues in step 954 where the currently calculated standing position ($x_c$, $y_c$) is compared to the initial calculated standing position ($x_{ci}$, $y_{ci}$). This calculation may be done by a linear comparison by separately determining the amount of change in the x and y components of the standing position value. Then, in step 956 these x and y values are compared to a twiddler's threshold value to determine if the change in the standing position may indicate twiddler's syndrome.

Preferably, a calculation may be performed as shown below:

$$P_t = \frac{(x_c^* x_{ci} + y_c^* y_{ci})}{(x_{ci}^2 + y_{ci}^2)}$$

to determine the correlation between the initial standing position value and the current standing position value. (Of course, while a two axes calculation is shown, the calculation can be expanded as previously described for a three axes embodiment.) A value of less than a predetermined Twiddler's Threshold value, e.g., 0.85, may indicate twiddler's syndrome. Accordingly, the process continues in step 958 where a Twiddler's Flag is set. The process then continues at step 435.

The status of the Twiddler's Flag may be sent to the external programmer 60 during a follow up visit of the patient to the physician. Preferably, the setting of the Twiddler's Flag can alert a physician of the potential prescience of twiddler's syndrome before damage to the lead has occurred.

The flow chart of FIG. 11 is only an exemplary method of monitoring for twiddler's syndrome. One of ordinary skill in the art would recognize that other methods could be used to monitor for trends in the calculated standing position. For example, one could monitor for changes in the calculated standing position between calculations or groups of calculations without actually storing the first post implantation value. All such methods are considered to be within the scope of the present invention.

Although the invention has been described with reference to particular embodiments, it is to be understood that these embodiments are merely illustrative of the application of the principles of the invention. For instance, this method can also be used to alter the defibrillation parameters in an implantable cardioverter/defibrillator unit. Accordingly, the embodiments described in particular should be considered exemplary, not limiting, with respect to the following claims.

What is claimed is:

1. A cardiac stimulation device comprising:
   means for sensing activity level and body position and for generating signals indicative of activity level and body position of a patient's body; and
   a controller that is adapted to be coupled to the means for sensing to receive the activity and position signals, wherein the controller is operative to process the activity and position signals to determine a standing position during an initial phase, and that, in a subsequent phase, is operative to compare the activity and position signals with the determined standing position to determine a patient position.

2. The device of claim 1, wherein the means for sensing comprises at least one sensor that generates both activity and position signals.

3. The device of claim 1, wherein the means for sensing comprises at least two sensors, wherein at least one of the sensors senses activity level and at least one of the sensors senses body position.

4. The device of claim 1, wherein the means for sensing comprises at least two sensors, wherein each of the at least two sensors is operative to sense activity level and body position.

5. The device of claim 1, wherein the controller is further operative to determine a stimulation rate based upon activity level and body position.

6. An implantable cardiac stimulation device, comprising:
   a sensor that senses body position of a patient;
   a detector that detects when the patient is in an active state;
   a signal processing circuit, coupled to the sensor and the detector, that automatically measures the patient's body position when the patient is detected in the active state and generates a standing position value based on the measured body position;
   a memory that stores the standing position value; and
   a controller, coupled to the detector, the memory and the pulse generator, configured to determine a current body position of the patient relative to the stored standing position value, and further configured to adapt a stimulation therapy based upon the patient's current body position.

7. The stimulation device of claim 6, wherein the detector comprises:
   an exercise state sensor that senses exercise state of the patient; and
   wherein the detector further detects when the patient's exercise state exceeds the standing threshold.

8. The stimulation device of claim 6, wherein the detector comprises:
   an activity sensor that senses activity level of the patient; and
   wherein the detector further detects when the patient's activity level exceeds the standing threshold.

9. The stimulation device of claim 6, wherein:
   the sensor is configured to sense resting and active states of the patient; and
   the detector further detects when the patient is not in the resting state.

10. The stimulation device of claim 6, wherein:
the sensor senses a diurnally varying parameter of the patient and monitors the variance of the diurnally varying parameter; and
wherein the detector further detects that the patient is in a wake state when the variance of the diurnally varying parameter is greater than a predetermined threshold.

11. The stimulation device of claim 6, further comprising:
a first sensor positioned along a first sensor axis, x, and configured to deliver a first signal having a DC position signal component indicative of the patient's body position along the first sensor axis and an AC activity level component indicative of activity of the patient's body position along the first sensor axis; and
a second sensor positioned along a second sensor axis, y, essentially orthogonal to the first sensor axis, and configured to deliver a second signal having a DC position signal component indicative of the patient's body position along the second sensor axis and an AC activity level component indicative of activity of the patient's body position along the second sensor axis.

12. The stimulation device of claim 6, wherein the detector correlates the current body position to the stored standing position via an equation:

$$P = \frac{(x^* x_c + y^* y_c)}{(x_c^2 + y_c^2)}$$

wherein:
x is the current body position signal from the first accelerometer along the first sensor axis;
y is the current body position signal from the second accelerometer along the second sensor axis;
$x_c$ is stored standing position along the first sensor axis; and
$y_c$ is stored standing position along the second sensor axis.

13. The stimulation device of claim 12, wherein the detector is operative to detect that the patient is standing when the projection value (P) is greater than a predetermined threshold, and that the patient is not standing when the projection value (P) is less than the predetermined threshold.

14. A cardiac stimulation device comprising:
at least one sensor that is operative to sense activity level and body position and further operative to generate signals indicative of activity level and body position of a patient's body; and
a controller that is adapted to be coupled to the at least one sensor to receive the activity and position signals, wherein the controller is operative to process the activity and position signals to determine a standing position during an initial phase, and that, in a subsequent phase, is operative to compare the activity and position signals with the determined standing position to determine a patient position.

15. The device of claim 14, wherein the at least one sensor comprises a single sensor that generates activity and position signals.

16. The device of claim 14, wherein the at least one sensor comprises at least two sensors, wherein at least one of the sensors senses activity level and at least one of the sensors senses body position.

17. The device of claim 14, wherein the at least one sensor comprises at least two sensors, wherein each of the at least two sensors is operative to sense activity level and body position.

18. The device of claim 14, wherein the controller is further operative to determine a stimulation rate based upon activity level and body position.

* * * * *